United States Patent [19]

Winkelmann et al.

[11] 4,105,763
[45] Aug. 8, 1978

[54] 1-METHYL-2-(PHENYL-OXYMETHYL)-5-NITRO-IMIDAZOLES

[75] Inventors: Erhardt Winkelmann, Kelkheim, Taunus; Wolfgang Raether, Dreieichenhain, both of Fed. Rep. of Germany

[73] Assignee: Hoechst Aktiengesellschaft, Frankfurt am Main, Fed. Rep. of Germany

[21] Appl. No.: 734,765

[22] Filed: Oct. 22, 1976

[51] Int. Cl.² ............... A61K 31/415; C07D 233/95; A61K 31/535; C07D 413/12
[52] U.S. Cl. .................. 424/246; 260/293.7; 542/406; 544/60; 544/139; 548/336; 548/339; 424/248.56; 424/267; 424/273 R

[58] Field of Search .............. 260/240 A, 240 G, 309, 260/293.7, 247.5 E, 243 B; 424/273, 248.56, 246, 267

[56] References Cited

U.S. PATENT DOCUMENTS

| | | | |
|---|---|---|---|
| B 484,067 | 2/1976 | Rufer et al. | 260/240 A |
| 3,951,963 | 4/1976 | Winkelmann et al. | 260/309 |
| 3,952,007 | 4/1976 | Rufer et al. | 260/309 |
| 3,993,469 | 11/1976 | Regel et al. | 260/309 |

*Primary Examiner*—Natalie Trousof
*Attorney, Agent, or Firm*—Curtis, Morris & Safford

[57] ABSTRACT

New 1-methyl-2-(phenyl-oxymethyl)-5-nitro-imidazoles are disclosed as well as a process for their manufacture. The new compounds are suitable for the treatment of protozoal diseases and show a marked activity against helminths, ectoparasites and ticks.

6 Claims, No Drawings

1-METHYL-2-(PHENYL-OXYMETHYL)-5-NITRO-IMIDAZOLES

The present invention relates to 1-methyl-2-(phenyl-oxymethyl)-5-nitro-imidazoles and process for preparing them.

1-(2-Hydroxyethyl)-2-methyl-5-nitro-imidazole (Metronidazol) is used for the treatment of protozoal diseases, such as trichomoniasis and amoebiasis.

The present invention provides 1-methyl-2-(phenyl-oxymethyl)-5-nitro-imidazoles of the formula I

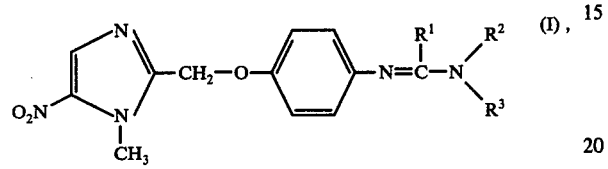

wherein $R^1$, $R^2$, $R^3$ can be identical or different and represent hydrogen, straight-chain or branched alkyl having from 1 to 4 carbon atoms, such as methyl, ethyl, propyl, isopropyl, butyl, isobutyl, or in which $R^1$ and $R^2$ as alkylene chain having from three to five carbon atoms, together with the nitrogen and carbon atoms of the amidino group, are constituents of a pyrrolidine, piperidine or hexamethylene-imine ring, or in which $R^2$ and $R^3$ as alkylene chain having four or five carbon atoms, together with the nitrogen atom of the amidino group, can be consituents of a pyrrolidine, piperidine, morpholine, or thiomorpholine ring, as well as the salts of these compounds (I) with a physiologically tolerable acid.

The invention also provides a process for the preparation of 1-methyl-2-(phenyl-oxymethyl)-5-nitro-imidazoles of the formula (I) as well as of the salts thereof with a physiologically tolerable acid, which comprises (A) reacting 1-methyl-2-(4-aminophenyl-oxymethyl)-5-nitroimidazole of the formula II

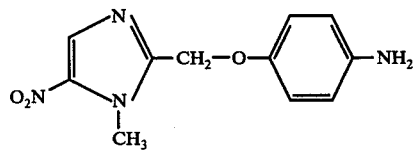

(a) with a carboxylic acid amide, a carboxylic acid thioamide, a lactam or a thiolactam of the formula III

wherein Z is oxygen or sulfur, and $R^1$, $R^2$ and $R^3$ have the meanings specified as above, in the presence of a condensing agent, or (b) with an acetal of a carboxylic acid amide or of a lactam of the formula IV

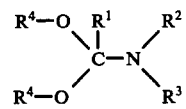

wherein $R^1$, $R^2$, $R^3$ have the meanings specified as above, and $R^4$ stands for methyl or ethyl, or (B) reacting a 1-methyl-2-halogenomethyl-5-nitro-imidazole of the formula V

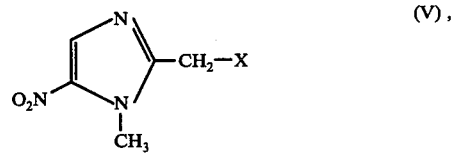

wherein X is a halogen atom, such as fluorine, chlorine, bromine, iodine, or an acyloxy group, such as acetyloxy, propionyloxy, butyryloxy, benzoyloxy, nitrobenzoyloxy, toloyloxy, or an aryl-sulfonyloxy group, such as benzoylsulfonyloxy, toluene-sulfonyloxy, nitrobenzene-sulfonyloxy, with a 4-amidinophenol or with the alkali metal or ammonium salt thereof of the formula VI

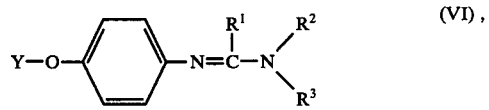

wherein Y represents hydrogen, an alkali metal, in particular sodium or potassium, or ammonium, and optionally adding a corresponding acid.

The starting compounds of the formula II may be prepared by reacting 1-methyl-2-chloromethyl-5-nitro-imidazoles of the formula V with 4-acylaminophenols or the alkali metal salts thereof and by saponifying the condensation product formed to give the free amine.

The starting compounds of the formula V may be prepared by reacting 1-methyl-2-hydroxymethyl-5-nitro-imidazole with the corresponding acid chlorides.

The starting compounds of the formula VI may be prepared by reacting 4-aminophenol with carboxylic acid amides of the formula III.

As starting compounds of the formula III (carboxylic acid amides and thioamides) there may be mentioned, for example, formamide, thioformamide, N-methyl-, N-ethyl-, N-propyl-, N-isopropyl-, N-butyl-, N-isobutyl, N,N-dimethyl-, N,N-diethyl-, N,N-dipropyl-, N,N-diisopropyl-, N,N-dibutyl-, N,N-diisobutylformamide, -thioformamide, -acetamide, -thioacetamide, -propionamide, -thiopropionamide, -butyramide, -thiobutyramide, -valeramide, -thiovaleramide, moreover, N-formyl-, N-acetyl-, N-propionyl-, N-butyryl-, N-valeryl-pyrrolidine, -piperidine, -morpholine, -thiomorpholine.

As further starting compounds of the formula III (lactams and thiolactams) there may be mentioned, for example, butyrolactam (pyrrolidone-2), valerolactam (piperidone-2), caprolactam (2-oxohexamethylene-imine), butyro-, valero-, caprothiolactam, N-methyl-, N-ethyl-, N-propyl-, N-butyl-butyro-, -valero-, -caprolactam, -butyro-, -valero-, -capro-thiolactam.

As starting compounds of the formula IV there may be mentioned, for example, formamide, N-methyl-, N-ethyl-, N-propyl-, N-isopropyl-, N-butyl-, N-isobutyl-, N,N-dimethyl-, N,N-diethyl-, N,N-dipropyl-, N,N-diisopropyl-, N,N-dibutyl-, N,N-diisobutylformamide-, -acetamide-, -propionamide-, -butyramide-, -valeramide-, dimethyl-, diethyl-acetal, moreover, N-formyl-, N-acetyl-, N-propionyl-, N-butyryl-, N-valerylpyrrolidine-, -piperidine-, -morpholine-, -thiomorpholine-, dimethyl-, diethyl-acetal, butyrolactam-, (pyrrolidone-2), valerolactam-, (piperidone-2), caprolactam-, (2-oxohexamethylene-imine), butyro-, valero-, capro-thiolactam-, N-methyl-, N-ethyl-, N-propyl-, N-butyl-butyro-, -valero-, -capro-lactam-, -butyro-, -valero-, -capro-thiolactam-, dimethyl-, -diethyl- acetal.

As starting compounds of the formula V there may be mentioned, for example, 1-methyl-2-chloro-, -2-bromo-, -2-iodomethyl-5-nitro-imidazole, 1-methyl-2-acetyloxy-, -2-benzoyloxy-, -2-(4-nitrobenzoyloxy)-, 2-toluene-sulfonyloxy-methyl-5-nitro- imidazole.

As starting compounds of the formula VI there may be mentioned, for example, 4-amino-, -methylamino-, -ethylamino-, -propylamino-, -isopropylamino-, -butylamino-, -isobutylamino-, -dimethylamino-, -diethylamino-, -di-n-propylamino-, -diisopropylamino-, -di-n-butylamino-, -diisobutylamino-, -pyrrolidino-, -piperidino-, -morpholino-, -thiomorpholino-methyleneimino-, -1-ethylene-imino-, -1-propylene-imino-phenol, as well as 4-(pyrrolidone-2-imino)-, -(piperidone-2-imino)-, -(2-oxohexamethylene-imino-2-imino)-, -(1-methyl-, 1-ethyl-, 1-propyl-, 1-butyl-pyrrolidone-, -piperidone-, -2-oxohexamethyleneimino-2-imino)-phenol.

The reactions according to the variants A) and B) of the preparation process are suitably carried out in equimolar amounts of the respective starting compounds. In the case of volatile reactants, however, excess amounts are recommended. The reactions are advantageously carried out in a solvent or distributing agent, however, certain reactions may also be carried out without a solvent or distributing agent, as indicated below.

As solvents or distributing agents there may be mentioned, for example:

For the process (Aa), aromatic, optionally halogenated hydrocarbons, such as benzene, toluene, xylene, chlorobenzene, dichlorobenzene, trichlorobenzene, chlorinated aliphatic hydrocarbons, such as methylene chloride, chloroform, aliphatic ethers, such as di-isopropylether, ethylene-glycol-dimethylether, -diethylether, diethylene-glycol-dimethylether, tetrahydrofurane, and dioxane.

It is particularly advantageous to use excess amounts of the carboxylic acid amides or lactams of the formula III used for the reaction. The excess may optionally be recovered in the processing of the reaction mixture.

For the process (Ab) there are mentioned alcohols, such as methanol, ethanol, propanol, butanol, methoxyethanol, ethoxyethanol, or most advantageously, an excess amount of the acetals of the carboxylic acid amides or of the lactams of the formula IV used for the reaction.

For the process (B) there are mentioned alcohols, such as methanol, ethanol, propanol, isopropanol, butanol, methoxyethanol, ethoxy-ethanol; ketones, such as acetone, methylethylketone, methylbutyl-ketone; amides, such as dimethylformamide, diethylformamide, dimethylacetamide, N-methyl-pyrrolidone, tetramethylurea, hexamethyl-phosphoric acid-triamide; furthermore, dimethylsulfoxide.

The reactions according to process (Aa) are advantageously carried out in the presence of a condensing agent. As condensing agents there may be mentioned preferably inorganic and organic acid halides, for example, thionylchloride, phosphorus trichloride, phosphorus pentachloride, phosphoroxychloride, chlorosulfonic acid, phosgene, oxalylchloride, chloroformic acid-alkylester, benzoylchloride, benzene-sulfonic acid-chloride, 4-toluene-sulfonic acid-chloride.

If for the reaction according to process (Aa), use is made of carboxylic acid thioamides and/or thiolactams, the use of a sulfur-binding agent is also recommended. As sulfur-binding agents there are mentioned, for example, heavy metal oxides, such as mercury oxide and lead oxide.

The reaction components according to process (Aa) are suitably reacted in equimolar amounts. The three latter components, in particular the carboxylic acid amides and thioamides, lactams and thiolactams, may also advantageously be used in excess amounts.

For the process variant (B) the use of an acid-binding agent is recommended, if the free phenols of the formula VI are used. As acid-binding agents there are mentioned bases, such as triethyl-amine or pyridine, as well as alkali metal and alkaline earth metal carbonates and -bicarbonates, -hydroxides and -alkoxides, for example, -methoxides, -ethoxides, and -butoxides.

For both steps of the process variants (A) and (B) the reaction temperatures are in the range of from 0° to 100° C, preferably from 25° to 80° C.

Depending on the process variant and on the range of temperature, the reaction times are in a range of from a few minutes to several hours.

The reaction products prepared according to process (Aa) are obtained in the form of their salts. They may be isolated as such or may optionally be converted into the free bases by alkalizing the aqueous solutions.

In order to alkalize said solutions, use is commonly made of strong bases, such as ammonia, sodium carbonate, potassium carbonate, sodium hydroxide, potassium hydroxide, or the aqueous solutions thereof. The bases which have been set free may again be converted into salts by way of physiologically tolerable acids.

As physiologically tolerable acids there are mentioned, for example, halogen hydracids, in particular hydrochloric acid, moreover, sulfuric acid, phosphoric acid, acetic acid, propionic acid, lactic acid, and tartaric acid.

If necessary, the reaction products may be purified by a recrystallization from a suitable solvent or solvent mixture.

The novel compounds of formula I are well compatible and are suitable for the treatment of protozoal diseases in mammals, as they are caused, for example, by infections with *Trichomonas vaginalis* and *Entamoeba histolytica*. Besides, they show a marked activity against helminths, ectoparasites and ticks.

The novel compounds can be administered orally or locally. The dosage unit for oral administration is given in the usual forms for pharmaceutical preparations, for example, tablets or capsules containing, per daily dosage unit, from about 10 to 750 mg of the active substance in combination with a usual carrier substance and/or constituent. For local application, there may be used, for example, jellies, creams, ointments or suppositories.

The following Examples serve to illustrate the invention.

EXAMPLES OF PREPARATION:

Process (Aa)

EXAMPLE 1;

(1.1)
1-Methyl-2-(4-dimethylamino-methylene-imino-phenyl-oxymethyl)-5-nitro-imidazole 248 Grams (1 mole) of 1-methyl-2-(4-aminophenyl-oxymethyl)-5-nitro-imidazole were dissolved in 1250 ml of dimethylformamide. At a temperature of from 30° to 40° C, 154 g (1 mole) of phosphoroxichloride were added dropwise, while stirring, to this mixture. Subsequently the reaction mixture was continued to be stirred for another 2 hours at 25° C. The final product was precipitated, while stirring, in the form of a salt, by adding 2.5 l of methylene chloride, it was then suction-filtered, washed with methylene chloride, suction-dried, dissolved in water, alkalized with aqueous concentrated ammonia, and the free base was shaken out several times with methylene chloride. The combined extracts were dried with sodium sulfate, were then evaporated, and the residue was recrystallized from alcohol, while adding charcoal. According to this method, 252 g (83% of the theory) of 1-methyl-2-(4-dimethylamino-methylene-imino-phenyl-oxymethyl)-5-nitroimidazole were obtained in the form of yellow crystals having a melting point of 145° C.

From the free base, the hydrochloride having a melting point of 187° C and having the form of slightly yellowish crystals could be prepared according to common methods, by using molar amounts of alcoholic hydrochloric acid.

The 1-methyl-2-(4-aminophenyl-oxymethyl)-5-nitroimidazole (orange red crystals, m.p. 152° C) used as starting compound could be prepared by saponifying 1-methyl-2-(4-acetaminophenyl-oxymethyl)-5-nitro-imidazole by means of 40% sulfuric acid (2 hours, 80° to 90° C), in a yield of 85%.

The 1-methyl-2-(4-acetaminophenyl-oxymethyl)-5-nitroimidazole (pale yellow crystals, m.p. 163° C) used for the preparation of the starting compound could be obtained by reacting molar amounts of 4-acetamino-phenol with 1-methyl-2-chloromethyl-5-nitro-imidazole in dimethylformamide (for 1 hour at 30° to 40° C), in the presence of potassium carbonate, in a yield of 95%.

The preparation of 1-methyl-2-chloromethyl-5-nitroimidazole has been described in German Offenlegungsschrift No. 1.595.929; it was effected by reacting the 1-methyl-2-hydroxymethyl compound with thionyl chloride.

It is also possible to use 1-methyl-2-benzoyloxymethyl-5-nitro-imidazole or 1-methyl-2-(4-nitrobenzoyloxymethyl)-5-nitro-imidazole instead of 1-methyl-2-chloromethyl-5-nitro-imidazole, the former compounds being obtained from the 1-methyl-2-hydroxymethyl compound with benzoylchloride and/or 4-nitrobenzoylchloride.

According to the process described in Example 1, the following compounds were obtained:

(1.2) From 1-methyl-2-(4-aminophenyl-oxymethyl)-5-nitroimidazole (APNI) and formamide, 1-methyl-2-(4-aminomethyleneimino-phenyl-oxymethyl)-5-nitro-imidazole;

(1.3) from APNI and N-methyleneformamide, 1-methyl-2-(4-methylamino-methyleneimino-phenyloxymethyl)-5-nitro-imidazole;

(1.4) from APNI and N-ethylformamide, 1-methyl-2-(4-ethylamino-methyleneimino-phenyloxymethyl)-5-nitro-imidazole;

(1.5) from APNI and N-n-propylformamide, 1-methyl-2-(4-n-propylamino-methyleneimino-phenyloxymethyl)-5-nitro-imidazole;

(1.6) from APNI and N-isopropylformamide, 1-methyl-2-(4-isopropylamino-methyleneimino-phenyloxymethyl)-5-nitroimidazole;

(1.7) from APNI and N-n-butylformamide, 1-methyl-2-(4-n-butylamino-methyleneimino-phenyloxymethyl)-5-nitro-imidazole;

(1.8) from APNI and N-isobutylformamide, 1-methyl-2-(4-isobutyl-amino-methyleneimino-phenyloxymethyl)-5-nitroimidazole;

(1.9) from APNI and N-diethylformamide, 1-methyl-2-(4-diethylamino-methyleneimino-phenyloxymethyl)-5-nitro-imidazole, m.p. 120° C (hydrochloride m.p. 164° C);

(1.10) from APNI and N-di-n-propylformamide, 1-methyl-2-(4-di-n-propylamino-methyleneimino-phenyloxymethyl)-5-nitroimidazole;

(1.11) from APNI and N-diisopropylformamide, 1-methyl-2-(4-diisopropylamino-methyleneimino-phenyloxymethyl)-5-nitroimidazole;

(1.12) from APNI and N-di-n-butylformamide, 1-methyl-2-(4-di-n-butylamino-methyleneimino-phenyloxymethyl)-5-nitroimidazole;

(1.13) from APNI and N-diisobutylformamide, 1-methyl-2-(4-diisobutylamino-methyleneimino-phenyloxymethyl)-5-nitroimidazole;

(1.14) from APNI and N-formylpyrrolidine, 1-methyl-2-(4-pyrrolidino-methyleneimino-phenyloxymethyl)-5-nitro-imidazole, m.p. 135° C;

(1.15) from APNI and N-formylpiperidine, 1-methyl-2-(4-piperidino-methyleneimino-phenyloxymethyl)-5-nitro-imidazole, m.p. 104° C;

(1.16) from APNI and N-formylmorpholine, 1-methyl-2-(4-morpholino-methyleneimino-phenyloxymethyl)-5-nitro-imidazole, m.p. 145° C;

(1.17) from APNI and N-formylthiomorpholine, 1-methyl-2-(4-thiomorpholino-methyleneimino-phenyloxymethyl)-5-nitroimidazole;

(1.18) from 1-methyl-2-(4-aminophenyl-oxymethyl)-5-nitroimidazole (APNI) and acetamide, 1-methyl-2-(4-amino-1-ethyleneimino-phenyloxymethyl)-5-nitro-imidazole;

(1.19) from APNI and N-methylacetamide, 1-methyl-2-(4-methylamino-1-ethyleneimino-phenyloxymethyl)-5-nitro-imidazole;

(1.20) from APNI and N-ethylacetamide, 1-methyl-2-(4-ethylamino-1-ethyleneimino-phenyloxymethyl)-5-nitro-imidazole;

(1.21) from APNI and N-n-propylacetamide, 1-methyl-2-(4-n-propylamino-1-ethyleneimino-phenyloxymethyl)-5-nitro-imidazole;

(1.22) from APNI and N-isopropylacetamide, 1-methyl-2-(4-isopropylamino-1-ethyleneimino-phenyloxymethyl)-5-nitro-imidazole;

(1.23) from APNI and N-n-butylacetamide, 1-methyl-2-(4-n-butylamino-1-ethyleneimino-phenyloxymethyl)-5-nitro-imidazole;

(1.24) from APNI and N-isobutylacetamide, 1-methyl-2-(4-isobutylamino-1-ethyleneimino-phenyloxymethyl)-5-nitro-imidazole;

(1.25) from APNI and N-dimethylacetamide, 1-methyl-2-(4-dimethylamino-1-ethyleneimino-phenyloxymethyl)-5-nitro-imidazole, m.p. 137° C;

(1.26) from APNI and N-diethylacetamide, 1-methyl-2-(4-diethylamino-1-ethyleneimino-phenyloxymethyl)-5-nitro-imidazole, m.p. 92° C;

(1.27) from APNI and N-di-n-propylacetamide, 1-methyl-2-(4-di-n-propylamino-1-ethyleneimino-phenyloxymethyl)-5-nitroimidazole;

(1.28) from APNI and N-diisopropylacetamide, 1-methyl-2-(4-diisopropylamino-1-ethyleneimino-phenyloxymethyl)-5-nitroimidazole;

(1.29) from APNI and N-di-n-butylacetamide, 1-methyl-2-(4-di-n-butylamino-1-ethyleneimino-phenyloxymethyl)-5-nitroimidazole;

(1.30) from APNI and N-diisobutylacetamide, 1-methyl-2-(4-diisobutylamino-1-ethyleneimino-phenyloxymethyl)-5-nitroimidazole;

(1.31) from APNI and N-acetylpyrrolidine, 1-methyl-2-(4-pyrrolidino-1-ethyleneimino-phenyloxymethyl)-5-nitro-imidazole;

(1.32) from APNI and N-acetylpiperidine, 1-methyl-2-(4-piperidino-1-ethyleneimino-phenyloxymethyl)-5-nitro-imidazole;

(1.33) from APNI and N-acetylmorpholine, 1-methyl-2-(4-morpholino-1-ethyleneimino-phenyloxymethyl)-5-nitro-imidazole;

(1.34) from APNI and N-acetylthiomorpholine, 1-methyl-2-(4-thiomorpholino-1-ethyleneimino-phenyloxymethyl)-5-nitroimidazole;

(1.35) from 1-methyl-2-(4-aminophenyl-oxymethyl)-5-nitroimidazole (APNI) and propionamide, 1-methyl-2-(4-amino-1-propyleneimino-phenyloxymethyl)-5-nitro-imidazole;

(1.36) from APNI and N-methylpropionamide, 1-methyl-2-(4-methylamino-1-propyleneimino-phenyloxymethyl)-5-nitro-imidazole;

(1.37) from APNI and N-ethylpropionamide, 1-methyl-2-(4-ethylamino-1-propyleneimino-phenyloxymethyl)-5-nitroimidazole;

(1.38) from APNI and N-n-propylpropionamide, 1-methyl-2-(4-n-propylamino-1-propyleneimino-phenyloxymethyl)-5-nitroimidazole;

(1.39) from APNI and N-isopropylpropionamide, 1-methyl-2-(4-isopropylamino-1-propyleneimino-phenyloxymethyl)-5-nitroimidazole;

(1.40) from APNI and N-n-butylpropionamide, 1-methyl-2-(4-n-butylamino-1-propyleneimino-phenyloxymethyl)-5-nitroimidazole;

(1.41) from APNI and N-isobutylpropionamide, 1-methyl-2-(4-isobutylamino-1-propyleneimino-phenyloxymethyl)-5-nitroimidazole;

(1.42) from APNI and N-dimethylpropionamide, 1-methyl-2-(4-dimethylamino-1-propyleneimino-phenyloxymethyl)-5-nitroimidazole, m.p. 115° C;

(1.43) from APNI and N-diethylpropionamide, 1-methyl-2-(4-diethylamino-1-propyleneimino-phenyloxymethyl)-5-nitroimidazole;

(1.44) from APNI and N-di-n-propylpropionamide, 1-methyl-2-(4-di-n-propylamino-1-propyleneimino-phenyloxymethyl)-5-nitro-imidazole;

(1.45) from APNI and N-diisopropylpropionamide, 1-methyl-2-(4-diisopropylamino-1-propyleneimino-phenyloxymethyl)-5-nitro-imidazole;

(1.46) from APNI and N-di-n-butylpropionamide, 1-methyl-2-(4-di-n-butylamino-1-propyleneimino-phenyloxymethyl)-5-nitro-imidazole;

(1.47) from APNI and N-diisobutylpropionamide, 1-methyl-2-(4-diisobutylamino-1-propyleneimino-phenyloxymethyl)-5-nitro-imidazole;

(1.48) from APNI and N-propionylpyrrolidine, 1-methyl-2-(4-pyrrolidino-1-propyleneimino-phenyloxymethyl)-5-nitroimidazole;

(1.49) from APNI and N-propionylpiperidine, 1-methyl-2-(4-piperidino-1-propyleneimino-phenyloxymethyl)-5-nitroimidazole;

(1.50) from APNI and N-propionylmorpholine, 1-methyl-2-(4-morpholino-1-propyleneimino-phenyloxymethyl)-5-nitroimidazole;

(1.51) from APNI and N-propionylthiomorpholine, 1-methyl-2-(4-thiomorpholino-1-propyleneimino-phenyloxymethyl)-5-nitroimidazole;

(1.52) from APNI and pyrrolidone-2 (butyrolactam), 1-methyl-2-[4-pyrrolidino-2-imino)-phenyloxymethyl]-5-nitroimidazole;

(1.53) from APNI and 1-methylpyrrolidone-2, 1-methyl-2-[4-(1-methylpyrrolidino-2-imino)-phenyloxymethyl]-5-nitroimidazole, m.p. 130° C;

(1.54) from APNI and 1-ethylpyrrolidone-2, 1-methyl-2-[4-(1-ethylpyrrolidino-2-imino)-phenyloxymethyl]-5-nitroimidazole;

(1.55) from APNI and 1-propylpyrrolidone-2, 1-methyl-2-[4-(1-propylpyrrolidino-2-imino)-phenyloxymethyl]-5-nitroimidazole;

(1.56) from APNI and 1-butylpyrrolidone-2, 1-methyl-2[4-(1-butylpyrrolidino-2-imino)-phenyloxymethyl]-5-nitroimidazole;

(1.57) from APNI and piperidone-2 (valerolactam), 1-methyl-2-[4-(piperidino-2-imino)-phenyloxymethyl]-5-nitroimidazole, m.p. 141° C;

(1.58) from APNI and 1-methylpiperidone-2, 1-methyl-2-[4-(1-methylpiperidino-2-imino)-phenyloxymethyl]-5-nitroimidazole;

(1.59) from APNI and 1-ethylpiperidone-2, 1-methyl-2-[4-(1-ethylpiperidino-2-imino)-phenyloxymethyl]-5-nitroimidazole;

(1.60) from APNI and 1-propylpiperidone-2, 1-methyl-2-[4-(1-propylpiperidino-2-imino)-phenyloxymethyl]-5-nitroimidazole;

(1.61) from APNI and 1-butylpiperidone-2, 1-methyl-2-[4-(1-butylpiperidino-2-imino)-phenyloxymethyl]-5-nitroimidazole;

(1.62) from APNI and 2-hexamethyleneimine (caprolactam), 1-methyl-2-[4-(2-oxohexamethyleneimino-2-imino)-phenyl-oxymethyl]-5-nitro-imidazole;

(1.63) from APNI and 1-methyl-2-oxohexamethyleneimine, 1-methyl-2-[4-(1-methyl-2-hexamethyleneimino-2-imino)-phenyloxymethyl]-5-nitroimidazole;

(1.64) from APNI and 1-ethyl-2-oxohexamethyleneimine, 1-methyl-2-[4-(1-ethyl-2-hexamethyleneimino-2-imino)-phenyloxymethyl]-5-nitroimidazole;

(1.65) from APNI and 1-propyl-2-oxohexamethyleneimine, 1-methyl-2-[4-(1-propyl-2-hexamethyleneimino-2-imino)-phenyloxymethyl]-5-nitroimidazole;

(1.66) from APNI and 1-butyl-2-oxohexamethyleneimine, 1-methyl-2-[4-(1-butyl-2-hexamethyleneimino-2-imino)-phenyl-oxymethyl]-5-nitroimidazole.

Example for process variant (A.b)

(2.1)
1-Methyl-2-(4-dimethylamino-methyleneimino-phenyl-oxymethyl)-5-nitro-imidazole 24.8 g (0.1 mol) of 1-methyl-2-(4-aminophenyl-oxymethyl)-nitro-imidazole were suspended in 250 ml of pyridine, 25 g (excess) of dimethylformamide-diethyl acetate were added and the reaction mixture was heated under reflux for 3 hours. The reaction medium pyridine was then distilled off under reduced pressure, the residue was recrystallized from alcohol while adding charcoal. According to this process, 24.0 g (79% of the theory) of 1-methyl-2-(4-dimethylamino-methylene-imino-phenyl-oxymethyl)-5-nitro-imidazole were obtained; which melted at 145° C.

Example for process variant (B)

(3.1)
1-Methyl-2-(4-dimethylamino-methylene-imino-phenyl-oxymethyl)-5-nitro-imidazole 17.55 g (0.1 mol) of 1-methyl-2-chloromethyl-5-nitro-imidazole were dissolved in 150 ml of dimethyl formamide, 16.4 g (0.1 mol) of 4-dimethylamino-methyleneimino-phenol (melting point 199° C) were added, 10.8 g (0.2 mol) of sodium methylate were added to the reaction mixture and the reaction mixture was heated to 40° C for 1 hour. Then, the solution was poured on to ice water, the precipitate was filtered off and recrystallized from alcohol while adding charcoal. According to this process, 22.7 g (67% of the theory) of 1-methyl-2-(4-dimethyl-amino-methyleneimino-phenyl-oxymethyl)-5-nitro-imidazole were obtained, which melted at 145° C.

The preparation of the 4-dimethyl-amino-methyleneimino-phenol used as starting substance is described in the U.S. Pat. No. 3,184,482, example 48.

The substances according to Examples 1.2 to 1.66 can be prepared according to the process variant (A.b) in analogy to Example 2.1 and according to the process variant (B.) in analogy to Example 3.1.

What is claimed is:

1. A 1-methyl-2-(phenyl-oxymethyl)-5-nitro-imidazole of the formula I

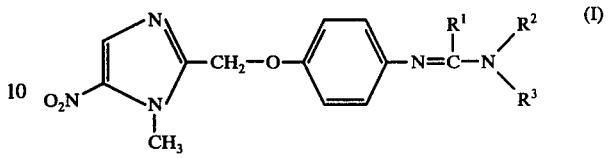

wherein $R^1$, $R^2$, $R^3$ are identical or different and represent hydrogen, straight-chain or branched alkyl of from 1 to 4 carbon atoms, or in which $R^1$ and $R^2$ represent an alkylene chain which, together with the nitrogen and carbon atoms to which it is attached, forms a pyrrolidine, piperidine or hexamethylene-imine ring, or in which $R^2$ and $R^3$ together with the nitrogen atom to which they are attached, form a pyrrolidine, piperidine, morpholine or thiomorpholine ring, as well as the salts thereof with a physiologically tolerable acid.

2. A compound as claimed in claim 1, which is 1-methyl-2-(4-dimethylamino-methyleneimino-phenyl-oxymethyl)-5-nitroimidazole.

3. A compound as claimed in claim 1, which is 1-methyl-2-(4-diethylamino-methyleneimino-phenyl-oxymethyl)-5-nitro-imidazole.

4. A compound as claimed in claim 1, which is 2-(4-morpholino-methyleneimino-phenyl-oxymethyl)-5-nitro-imidazole.

5. A pharmaceutical composition for the treatment of protozoa, helminths and ectoparasites in mammals consisting of an effective amount of a compound of formula I as claimed in claim 1, in admixture of conjunction with a pharmaceutically suitable carrier.

6. A method for the treatment of protozoa, helminths and ectoparasites in mammals which comprises administering an effective amount of a compound of the formula I as claimed in claim 1.

* * * * *